United States Patent
Sato

(10) Patent No.: US 7,053,173 B2
(45) Date of Patent: May 30, 2006

(54) POLYMERCAPTOPOLYPHENYL AND PROCESS FOR PREPARATION THEREOF

(75) Inventor: Ryu Sato, Iwate (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

(21) Appl. No.: 10/472,376

(22) PCT Filed: Apr. 15, 2002

(86) PCT No.: PCT/JP02/03736

§ 371 (c)(1),
(2), (4) Date: Sep. 23, 2003

(87) PCT Pub. No.: WO02/085846

PCT Pub. Date: Oct. 31, 2002

(65) Prior Publication Data

US 2004/0092775 A1    May 13, 2004

(30) Foreign Application Priority Data

Apr. 17, 2001 (JP) .............................. 2001-117800
Feb. 14, 2002 (JP) .............................. 2002-036586

(51) Int. Cl.
*C08G 75/00* (2006.01)
(52) U.S. Cl. ...................... 528/373; 528/391; 568/61; 568/38
(58) Field of Classification Search ................ 528/373, 528/391; 568/38, 61
See application file for complete search history.

(56) References Cited

FOREIGN PATENT DOCUMENTS

JP        8-20650      *  1/1996
WO        WO 00-41213  *  7/2000

* cited by examiner

*Primary Examiner*—Duc Truong
(74) *Attorney, Agent, or Firm*—Sherman & Associates

(57) ABSTRACT

Novel di-, tri-, or tetra-thiols or thiolates of biphenyl, biphenyl derivatives, terphenyl or terphenyl derivatives, as represented by general formula (A), wherein $M_1$ and $M_2$ are each independently selected from the group consisting of H, Na, Li and K, and $R_1$ to $R_7$ are each H or an organic group, with the proviso that $M_1$, $M_2$ and $R_1$ to $R_7$ may be the same or different from each other; $E_1$ and $E_2$ are $SM_3$ and $SM_4$ (wherein $M_3$ and $M_4$ are each selected from the same group as defined above for $M_1$ or $M_2$) or each a group selected from among those as defined above for $R_1$ to $R_7$; and n is 1 or 0, with the proviso that when n is 0, $E_1$ and $E_2$ are $SM_3$ and $SM_4$.

general formula A

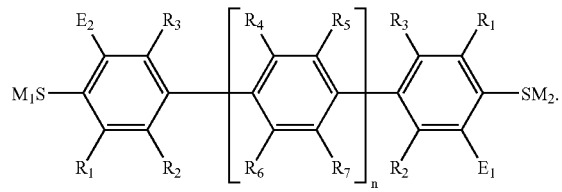

8 Claims, No Drawings

POLYMERCAPTOPOLYPHENYL AND PROCESS FOR PREPARATION THEREOF

FIELD OF THE INVENTION

The present invention relates to novel tri- or tetra- thiols or thiolates of biphenyl or biphenyl derivatives, terphenyl or terphenyl derivatives, and relates to a process for preparation of above mentioned thiols and thiolates.

BACKGROUND OF THE INVENTION

It is known that a compound having two or more mercapto groups [R—(SH)a, wherein R is an organic group of "a" valent such as alkylene group which can possess a branch group or arylene group] is used to synthesize the resin of high refractive index ($N_D^{20°\ C.} \geq 1.60$) by reacting with, for example, polyisocyanates (refer to JPS60-199016 Laid-open publication and JPS62-267316 Laid-open publication). As the related prior arts, in JPH8-269161 Laid-open publication, 2,2'-dimethylmercaptobiphenyl and 4,4'-dimercaptobiphenyl are reported as the biphenyl derivatives of dimethylmercapto compound.

And further, there is a description illustrating that the reacted components substituted with allyl group or halogen contributes to the improvement of refractive index.

Furthermore, it is known that the compounds having a thiol group can form a mono molecular film composed of above mentioned compounds on the surface of metal or on the surface of fine metal particles of metals, such as noble metal for example, Au, Pt, Ag or Pd and transition metal, in self-assembling manner by an electron force of S atom. Mono molecular film mentioned above is also converted to the film with various function by bonding a compound which imparts various function to the surface of said mono molecular film to an another end group of said compounds selected from a group consisting of thiol and other than thiol.

For example, a self assembling film is formed by using a compound with a functional group that reacts structural specifically (specifically, like as antigen-antibody reaction) and by combining said film with Quartz-Crystal Microbalance, and applying above mentioned idea e.g. for the method to detect DNA quantitatively has already proposed (Document 1; Kenichi Niikura et al. Chem. Letter 1996, 863–864).

Further, the following prior art has also proposed; which comprises (1) synthesizing PEG derivative by introducing a functional group (for example, mercapto group or polyamine group), via which the PEG derivative is loaded on the surface of ultra fine particles of metal, metal oxide or semi conductor to one end (for example, α-end) of a PEG and a functional group which can react with a functional compound such as antibody, protein or dye to another end (ω-end) of the PEG, and (2) loading the PEG derivative synthesized above on fine particles of metal, metal oxide or semi conductor to improve the dispersing stability and to posse (to be modified with) a functional group having the reactivity with a functional compound to the other end of PEG chain expanding from the surface (extends to the outer side) of fine particles to obtain a new dispersion stabilized complex [refer to Document 2; 48$^{th}$ Polymer forum (1999), October 6–8, at Niigata University, Igarashi Campus "Polymer Science, Abstracts" Vol. 48, No.14, 4113–4114, issued on Sep. 20, 1999].

The reactivity and function of above mentioned mercapto group indicates one of the importance aspects of the mercapto compound. The various functions of the mercapto group are further important, because functions of a compound can be enhanced by being converted to a polymercapto compound with higher mercapto group content.

In general, the circuit in which fine semi-conductor elements are assembled is prepared by printing a pattern of circuit on a silicon substrate and to produce the circuit corresponding to the printed pattern, namely, photolithographical technique is applied. With the advancement in technique, the circuit pattern becomes fine and the line which composes the circuit pattern also becomes fine, and it is necessary for the printing means based on the photolithographical technique to use shorter wavelength.

However, for the manufacturing the molecular scale transistor, it is said that the photolithographical technique can not apply no longer. Therefore, it is required for molecular scale transistor material to have the function to coordinate in self-assembling manner to a metal electrode with the electronics characteristic.

Recently, the technique to prepare a mono molecular electronics device is proposed. The technique described above comprise (1) employing a mono molecular which possesses groups which have bonding ability with an electrode, such as SH groups on ends and field-effect semi-conductor part, donor part, acceptor part, electric conductive part and insulating part in the monomolecular, (2) and assembled the monomolecular to each electrode by end SH groups depicted above to obtain a monomolecular electronic device [Document 5; U.S. Pat. No. 6,339,227 B1 publication (patented on Jan. 15, 2002)].

Further, for example, as OH group of 3,3'4,4'-tetrahydroxybiphenyl or 2,2',4,4'-tetrahydroxybiphenyl is used for the synthesis of polymer, the cross-linking or the function group reacting with other compound or with the group existing on the surface, so SH group has a possibility to have similar function. Therefore, each of SR groups of tetramercaptobiphenyl and the derivative thereof, and each of thiols or thiolates of tri- or tetra-thiols or thiolates of terphenyl or terphenyl derivative can respectively take part in various reactions, and it is obvious that the function of said compound can be improved along with the increase of the number of functional groups.

While, as the process for preparing an aromatic thiol, the process using a reaction of reducing an aromatic sulfochloride is most popular, and in reaction mentioned above, the combination of zinc dust and sulfuric acid (carried out at 0° C.), tin and hydrochloric acid, mixture of phosphorus, potassium iodide and phosphoric acid and lithium aluminium hydride can be used.

An object of the present invention is to provide a novel compound which has mercapto groups with more improved function depicted above. Further, to improve the variety of function of above mentioned compound, the skeletal structure to which thiols or thiolates are changed to terphenyl or terphenyl derivative and introducing three or more thiols or thiolates to the terphenyl or terphenyl derivative.

Therefore, it is important to find out a process to prepare the compound depicted above. The inventors of the present invention have found out the following methods for introducing said group with sulfur to an aromatic ring of biphenyl, terphenyl or derivatives thereof. That is, A. a method comprising (1) synthesizing 4,4'-biphenyldisulfonylchloride or 4,4'-terphenyldisulfonylchloride by reacting ClSO$_3$H with biphenyl or terphenyl, and (2) synthesizing di-thiol or thiolate by reacting lithium aluminium hydride with the product obtained by (1), B. a method comprising (1) synthesizing 4,4'-biphenyldisulfonylchloride according to the process (1) mentioned above in A, (2) synthesizing 4,4'-bis(N,N'-dimethylaminosulfonyl)-biphenyl by reacting dimethylamine (HNMe$_2$) with product obtained in (1), (3) synthesizing 4,4'-bis(N,N'-dimethylaminosulfonyl)-3,3'-dimethylcaptobiphenyl by reacting normalbutyllithium (n-BuLi) with the product obtained in (2), and further reacting simple substance of sulfur S$_8$ with the product obtained in former reaction, (4) synthesizing (2,2-dimethyl[3,4-d]-1,3,2-dithiastanolo) biphenyl by reacting LiAlH$_4$/NaBH$_4$ with product obtained in (3), and finally (5) synthesizing by introducing SH groups onto 3,3',4 and 4' carbon in biphenyl by reacting hydrogen chloride with product obtained in (3).

C. a method comprising (1) synthesizing 4,4'-biphenyldisulfonylchloride according to the process (1) mentioned above in A, (2) synthesizing 4,4"-bis(N,N'-dimethylaminosulfonyl)-terphenyl by reacting dimethylamine (HNMe$_2$) with product obtained in (1). (3) synthesizing 4,4'-bis(N,N'-dimethylaminosulfonyl)-3 and/or 3"-mercapto or dimethylmercaptoterphenyl by reacting normalbutyllithium (n-BuLi), and further reacting with simple substance of sulfur S$_8$ with product obtained in (2), and finally (4) synthesizing 3,3",4-trimercapto-1,1':4',1"-terphenyl, 3,3",4,4"-tetramercapto-1,1':4',1"-terphenyl or derivatives thereof by lithiumammoniumhydrate with product obtained in (3).

And the inventors of the present invention accomplished the object mentioned above.

The object of the present invention is to provide a novel tri- or tetrathiol or thiolate of biphenyltetrathiol and biphenyltetrathiol derivatives, or a novel tri- or tetrathiol or thiolate of terphenyl or terphenyl derivatives which can improve the variety of said tetrathiol or thiolate compound. By selecting terphenyl as skeletal structure to which thiols or thiolates are attached, the variety of molecular designed can be improved, for example, the length of electric conductive molecule becomes long and the number of carbon atoms to which a substituent can be introduced is increased. Then, possibilities of development of a functional material to be applied to various fields can be expected. The improvement of the length of chain with electro conductivity brings the abundance of mono molecule device mentioned above. And considering the development of a molecular scale device, the possibility of developing a novel device with triply terminals material can be expected by functionally assembling the present compounds between metal electrodes by coordinate bond. This element makes the application to a communication device or to an electronic device possible. Further, the possibility of the application to a rubber industry, an adhesive, a paints and so on, by using chemical characteristics of SH, becomes higher.

Especially, among the compounds of the present invention, the compound having 3 or 4 substituents of thiol or thiolate has not been reported yet except of the proposal by the inventors of the present invention. The introduction of 3 or 4 substituents of thiol groups means to introduce two thiol groups selectively to the adjacent sites each other, and so the development of the technique producing said compound was not easy.

DISCLOSURE OF THE INVENTION

The first one of the present invention is relating to tetrathiol or thiolate represented by general formula 1 and the method for producing thereof.

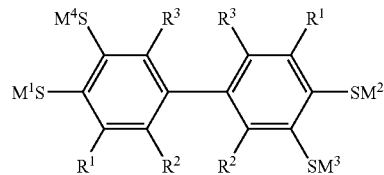

general formula 1

(in general formula 1, M$^1$, M$^2$, M$^3$ and M$^4$ can be selected independently from the group consisting of H, Na, Li and K. R$^1$, R$^2$ and R$^3$ are a group selected independently from the group consisting of H, substituted or not substituted alkyl group, substituted or not substituted phenyl group, naphthyl group, benzyl group, pyridyl group, substituted or not substituted alcoxy group, alcoxycarbonyl group, aldehyde group, nitroso group, nitro group, substituted or not substituted amino group, substituted or not substituted phenylazo group, alkylazo group, substituted or not substituted alkylthio group, substituted or not substituted phenylthio group, substituted or not substituted alkylsulfinyl group, phenylsulfinyl group, substituted or not substituted alkylsulfonyl group, phenyl sulfonyl group, divalent benzophenon residue, phenylether residue, alkylene group, cyclo alkylene group, pyridilene group, ester residue, carbonyl group and biphenylyl group, and R$^1$–R$^3$ on phenyl group can be same or can be different)

Further, the synthesis of the compound of general formula 1 mentioned above contains at least following processes (1)–(5), namely, using biphenyl or biphenyl derivatives as the starting material and (1) synthesizing 4,4'-biphenyldisulfonylchloride or derivatives thereof by reacting ClSO$_3$H with said starting material, (2) synthesizing 4,4"-bis(N,N'-dimethylaminosulfonyl)-biphenyl or derivatives thereof by reacting with dimethylamine with the compound obtained in (1), (3) synthesizing 4,4'-bis(N,N'-dimethylaminosulfonyl)-3,3'-dimercaptobiphenyl or derivatives thereof by reacting normalbutyllithium with the compound obtained in (2), and further reacting simple substance of sulfur S$_8$ with the product obtained in former reaction, (4) synthesizing bis(2,2-dimethyl[3,4-d]-1,3,2-dithiastanolo) biphenyl or derivatives thereof by reacting LiAlH$_4$/NaBH$_4$ with product obtained in (3), and then (5) reacting hydrogen chloride with product obtained in (4).

The second one of the present invention is relating to tri- or tetra-thiol or thiolate represented by general formula 2.

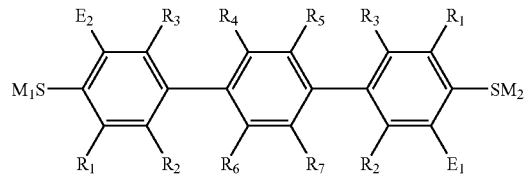

general formula 2

(in general formula 2, M$_1$ and M$_2$ are selected independently from the group consisting of H, Na, Li and K, R$_1$–R$_7$ are a group selected independently from the groups consisting of H, substituted or not substituted alkyl group, substituted or not substituted phenyl group, naphthyl group, benzyl group, pyridyl group, substituted or not substituted alcoxy group, alcoxycarbonyl group, aldehyde group, nitroso group, nitro group, substituted or not substituted amino group, substituted or not substituted phenylazo group, alkylazo group, substituted or not substituted alkylthio group, substituted or not substituted phenylthio group, substituted or not substituted alkylsulfinyl group, phenylsulfinyl group, substituted or not substituted alkylsulfonyl group, phenyl sulfonyl group, divalent benzophenon residue, phenylether residue, alkylene group, cyclo alkylene group, pyridilene group, ester residue, carbonyl group and biphenylyl group, and $R_1$–$R_7$ on phenyl group can be same or can be different.

$E_1$ and/or $E_2$ are $SM_3$ and/or $SM_4$ ($M_3$ and $M_4$ are a group independently selected from the group which defines afore mentioned $M_1$ or $M_2$) or a group selected independently from the group consisting of $R_1$–$R_7$]

Desirably the second one of the present invention is a compound represented by following chemical formulae 1–2.

chemical formula 1

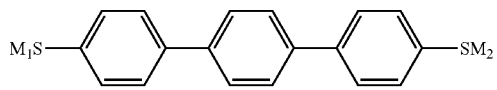

chemical formula 2

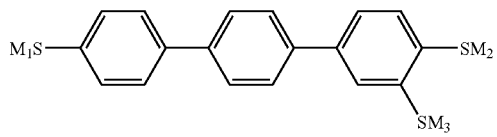

chemical formula 3

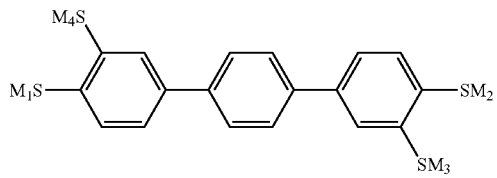

The third one of the present invention is a process for preparation of terphenyl, terphenyl derivatives containing in general formula 2 or dithiol or thiolate of terphenyl or terphenyl derivatives represented by chemical formula 1 mentioned above. It comprises (1) synthesizing 4,4"-terphenyldisulfonylchloride or derivatives thereof by reacting ClSO₃H with terphenyl or terphenyl derivatives and (2) reacting lithium ammonium hydroxyde with the product obtained by (1).

The fourth one of the present invention is a process for preparation of tri- or tetra-thiol or thiolate of terphenyl or terphenyl derivatives of compounds which are contained in the compounds represented by general formula 2 wherein $E_1$ or/and $E_2$ is a group defined said $SM_1$, chemical formula 2 or chemical formula 3, containing processes (1)–(4), namely, using terphenyl or terphenyl derivatives as the starting material and (1) synthesizing 4,4'-terphenyldisulfonylchloride or derivatives thereof by reacting ClSO₃H with said starting material, (2) synthesizing 4,4"-bis(N,N'-dimethylaminosulfonyl)-terphenyl or derivatives thereof by reacting dimethylamine with the compound obtained in (1), (3) synthesizing 4,4'-bis(N,N'-dimethylaminosulfonyl)-3, and/or 3"-mercapto or dimethylmercaptoterphenyl, by reacting normalbutyllithium with the compound obtained in (2), and further reacting simple substance of sulfur $S_8$ with the product obtained in former reaction, and then (4) reacting lithium ammonium hydroxyde with the product obtained by (3).

THE BEST EMBODIMENT TO CARRY OUT THE INVENTION

The present invention will be illustrated more in detail.

A. $M^1$, $M^2$, $M^3$, $M^4$, $M_1$ and $M_2$ in general formulae 1 and 2, chemical formulae 1–3 can be various kind of derivatives in relation with the uses of thiol or thiolate of the present invention. For example, thiols which is introduced into biphenyl or terphenyl can be used as an electrical conductive material by itself when arranged between electrical conductive metals such as gold or cupper. Therefore, it can be applied for an electrical connection for various electronic devices such as organic semiconductor, and transistor. In said case, the degree of electrical conductivity is considered to be controlled by adjusting the number of thiols introduced to biphenyl and terphenyl, namely, by using tetra-, and tri-thiol derivatives. Further, thiol group can be bonded to the surface of metal, nano size particles of metal or a semi conductor, and can impart various functions such as adherence with metal or can impart the functions which substituents of thiol derivatives have.

B. By an introduction of a substituent to sites of $R^1$–$R^5$, $R^1$–$R_7$ excepting the sites to which thiol or thiolate of diphenyl or terphenyl attached represented by general formula 1 or 2. In a case when the compound mentioned above apply to the electronic device, arrangement of the compound with thiols introduced between metals can be controlled precisely by the substituent introduced controlling the vicinal force such as van der Waals force.

By controlling arrangement of the molecules with thiols precisely, the application to an organic molecule device or to a transistor becomes possible. Further, various substituents are available depend on the use of a compound with thiols besides above mentioned electrical conductive feature. For example, the introduction of halogen can improve the feature such as refractive index or flame retardation, of the polycarbonate.

C. The process for synthesis of the compound included in general formula 1 is shown in schema 1.

schema 1

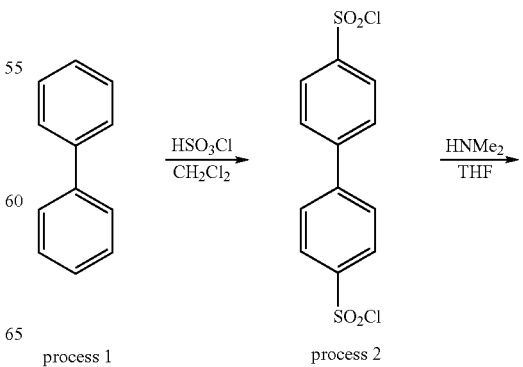

process 1    process 2

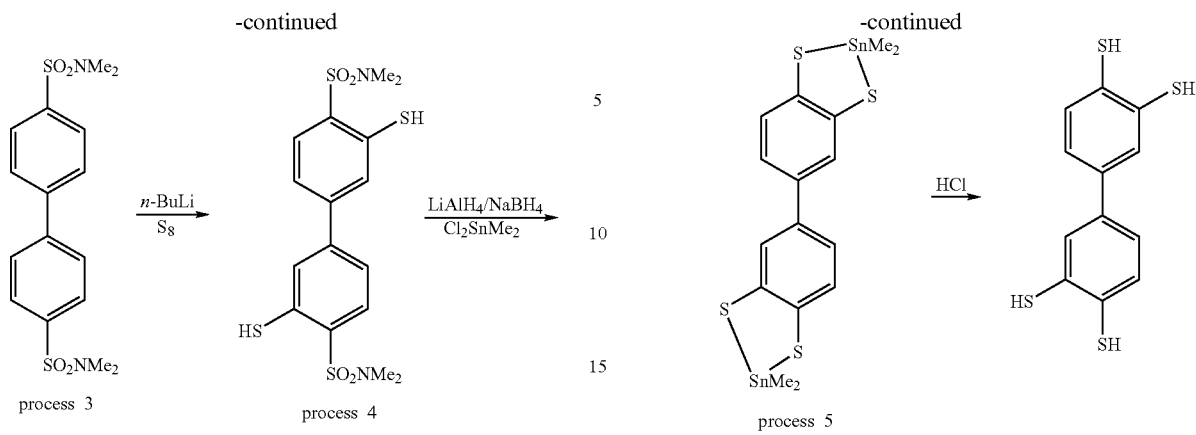
D. The process for synthesis of the compound included in general formula 2 is shown in schema 2.
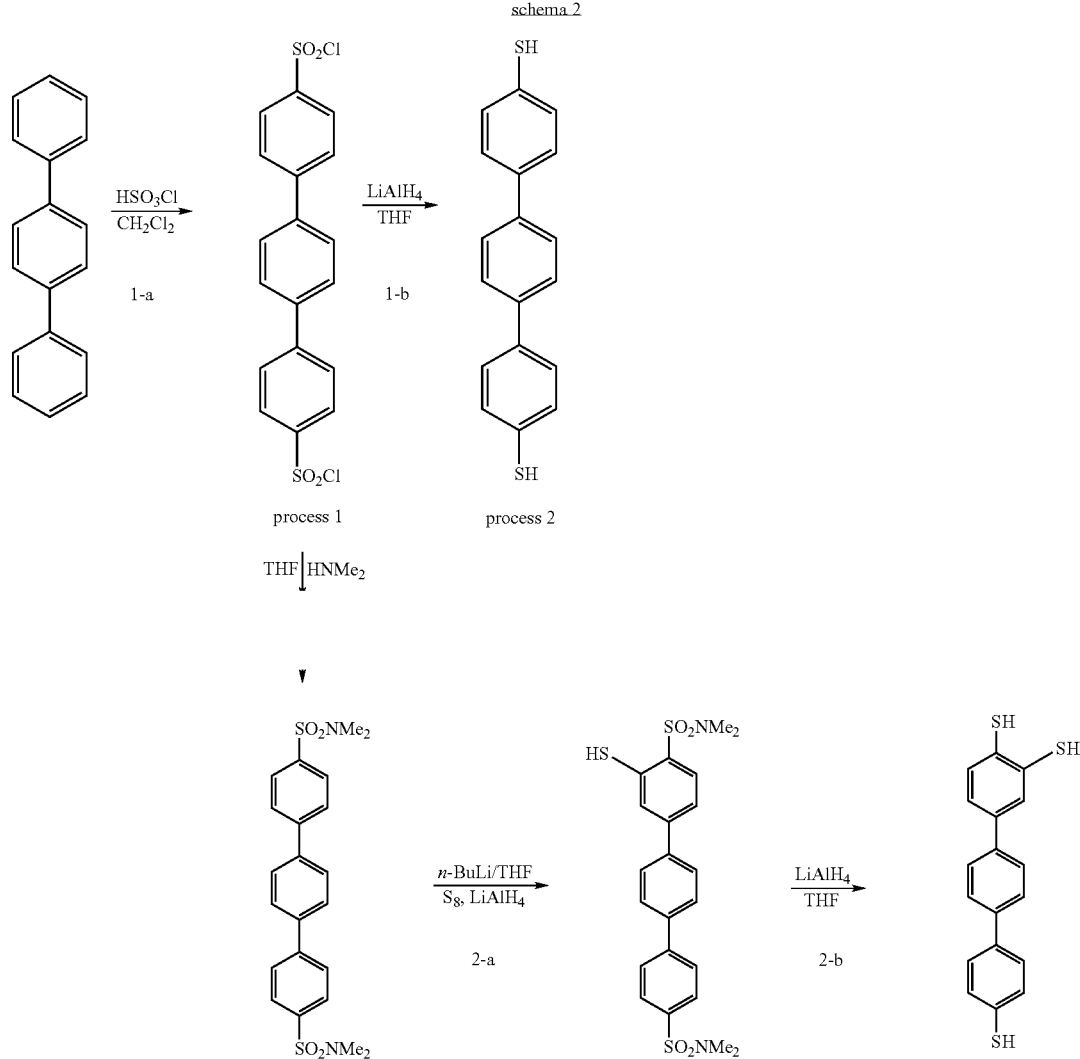

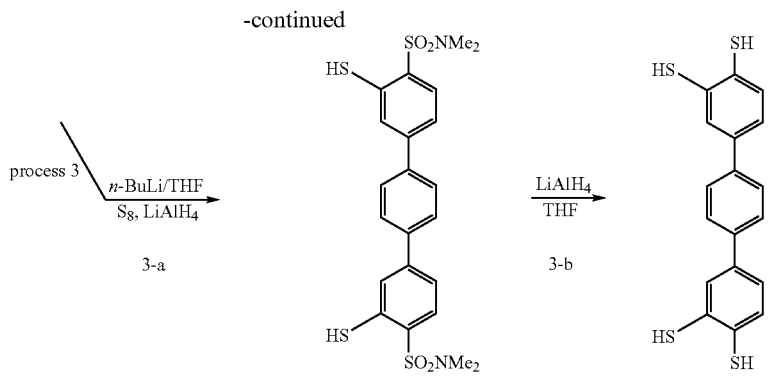

Process 1 is the process of synthesizing dithiol of terphenyl or terphenyl derivative (1-b), comprising (1) synthesizing 4,4"-disulfochloride of terphenyl(1-a) and (2) reducing obtained disulfochloride by LiAlH₄ (1-b).

Process 2 is the process of synthesizing terphenyl or terphenyl derivatives trithiol or thiolate, comprising (1) synthesizing 4,4"-bis(N,N'-dimethylaminosulfonyl)-terphenyl or derivatives thereof by reacting dimethylamine to 4,4"-disulfochloride, introducing thiol to 3 and 3" site (2-a) by reacting one equivalent weight of n-BuLi, simple substance of sulfur S₈ and lithium ammonium hydroxide with said dimethylaminosulfonyl obtained in former reactio, and (2) then reducing disulfochloride with lithium ammonium hydroxyde (2-b).

Process 3 is the process of synthesizing terphenyl or terphenyl derivatives trithiol or thiolate, comprising (1) reacting one equivalent weight of n-BuLi to introduce thiol to 3 and 3" site (3-a), and then (2) reducing disulfochloride with lithium ammonium hydroxyde (3-b).

EXAMPLES

The present invention will be illustrated more in detail according to the Examples. However, following Examples are intending to make the usefulness of the present invention more clearly and not intending to limit the scope of claims of the present invention.

Example 1

A. Synthesis of 4,4'-biphenyldisulfochloride (Process 1 of Schema 1: Chlorosulfonylation)

Under the nitrogen gas atmosphere, chloro sulfuric acid is diluted by adding chloro sulfuric acid (21.184 mmol) into methylene chloride (40 ml), and biphenyl (6.168 g, 40.00 mmol) is added gradually into a container in which diluted chloro sulfuric acid is contained keeping the temperature at 0° C., then stirred at the room temperature for 6 hours. The obtained reacted mixture is poured into brine, and deposited white insoluble is removed by suction filtration. Since the small amount of product is possible to be remained, the residue is washed well by methylene chloride. Then the filtrate is extracted by methylene chloride (150 ml×3), and the separated organic phase is dried up using magnesium sulfate. Solvent is vaporized off under vacuum condition, and the obtained crude product is isolated by a column chromatography (φ=50 mm, h=100 mm×2; CH₂Cl₂), further refined by recrystallization (CHCl₃) and 4,4'-biphenyldisulfonylchloride is obtained as a colorless crystal (8.201 g, 23.349 mmol, 58%) (compound A).

Physical properties of compound A: Melting point 206–207° C. (literature date: 205–208° C.).

1N NMR (400 MHz, CDCl₃), δ7.86 (d, j=8.5 Hz, 4H, ArH), 8.19 (d, j=8.5 Hz, 4H, ArH).

B. Synthesis of 4,4"-bis(N,N'-dimethylaminosulfonyl)biphenyl (Process 2 of Schema 1: Amidation)

To the tetrahydrofuran(THF) solution (20 ml) of 4,4'-biphenyldisulfonylchloride (7.788 g in 22.17 mmol), 50 ml of dimethylamine solution (10.567 ml, 106.416 mmol) is added, stirred at room temperature for 3 hours, then, water is added and stirred another 30 minutes. The obtained reacted solution is filtrated by suction filtration, and the residue is heat dried (50° C.) in a vacuum desiccator. THF is extracted from the filtrate by extraction using ether (50 ml) and transferred to an organic phase, then extracted by methylene chloride (50 ml×2), and the separated organic phase is dried using magnesium sulfate. Solvent is evaporated off under vacuum condition and the obtained crude product is refined by crystallization (CH₂Cl₂). Thus, 4,4"-bis(N,N'-dimethylaminosulfonyl) biphenyl is obtained as a colorless crystal (8.026 g, 21.78 mmol, quant.) (compound B).

Physical properties; Melting point is 244° C.; ¹H NMR (400 MHz, CDCl₃), δ2.77 (s, 12H, CH₃), 7.78 (d, j=8.3 Hz, 4H, ArH), 7.90(d, j=8.3 Hz, 4H, ArH); ¹³CNMR (101 MHz, CDCl₃), δ37.9, 127.9, 128.5, 135.5, 143.6; IR (KBr) 134.1, 1163 (SO₂) cm⁻¹.

C. Synthesis of 4,4"-bis(N,N'-dimethylaminosulfonyl)-3,3'-dimercapto biphenyl (Process 3 of Schema 1: Orthorethiolation-Sulfurization)

Under the nitrogen gas atmosphere, 2.47M of n-butyllithium (14.6 ml, 36.00 mmol) is added to absolute THF suspension (150 ml) of 4,4"-bis(N,N'-dimethylaminosulfonyl)-biphenyl (5.527 g, 10.00 mmol) and stirred at the room temperature for 2 hours, then simple substance of sulfur S₈ is added and further stirred another 3 hours. To the reaction solution, lithium aluminium hydride is added and stirred for 1 hour. The obtained reacted mixture is poured into ice water, and adjusted the pH to 1 or less by adding concentrated hydrochloric acid. THF is extracted from the solution by extraction using ether (50 ml) and transferred to an organic phase, then extracted by methylene chloride (50 ml×3), and the separated organic phase is dried up using magnesium sulfate. Solvent is evaporated off under vacuum condition and the obtained crude product is isolated by a column chromatography (φ=50 mm, h=100 mm×2; CHCl₃: AcOEt=5:1), further refined by crystallization (CHCl₃) and 4,4'-bis(N,N'-dimethylaminosulfonyl)-3,3'dimercaptobiphenyl is obtained as a yellowish crystal (5.001 g, 56 mmol, 77%) (compound C).

Physical properties of compound C: Melting point 171–172° C.: $^1$H NMR (400 MHz, CDCL$_2$), δ2.88 (s, 12H, CH$_3$), 4.85 (s, 12H, SH), 7.42 (dd, j=1.8, 8.3 Hz, 2H, ArH), 7.58 (d, j=1.8 Hz, 2H, ArH), 7.98 (d, j=8.3 Hz, 2H, ArH), $^{13}$CNMR (101 MHz, CDCl$_3$) δ37.6, 124.0, 130.5, 131.9, 133.6, 135.1, 142.9; IR (KBr) 2548 (SH), 1342, 1164 (SO$_2$)cm$^{-1}$; MS (70 eV)m/z432 (M$^+$); Anal. Calculated value, C$_{16}$H$_{20}$N$_2$O$_4$S$_4$: C, 44.42; H, 4.66, N, 6.48%. Measured value: C, 44.05; H, 4.36; N, 6.38%.

D. Synthesis of bis(2,2-dimethyl[3,4-d]-1,3,2-dithiastannolo)biphenyl (Process 4 of Schema 1: Stanylization)

To the pre-dried THF solution (75 ml) of 4,4"-bis(N,N'-dimethylamino sulfonyl)-3,3'-dimercaptobiphenyl (1.298 g, 3.000 mmol), lithium aluminium hydroxide (1.366 g, 36.00 mmol) is added at 0° C., and the reacting solution is refluxed for 24 hours. The obtained reacted mixture is poured into ice water, and adjusted the pH of the solution to 1 or less by adding concentrated hydrochloric acid so as to acidificate the solution. The solution is extracted by methylene chloride (50 ml×3), and the separated organic phase is dried using magnesium sulfate. Solvent is evaporated off under vacuum condition and obtained insoluble product is dried by vacuum drying so that the solvent is completely removed. To the solution of pre-dried THF (60 ml)/pre-dried EtOH (12 ml) of said insoluble product, sodium borohydride is added at 0° C., stirred for 30 minutes at the room temperature. Then, water is added, further, concentrated hydrochloric acid is added and neutralized (pH 4–7). Immediately after, dimethyltin dichloride is added and stirred for 30 minutes at room temperature. The solution is extracted by methylene chloride (50 ml×3), and the separated organic phase is dried using magnesium sulfate. Solvent is evaporated off under vacuum condition and the obtained crude product is isolated by a column chromatography (φ=35 mm, h=80 mm; CHCl$_3$), further refined by crystallization (THF-CHCl$_3$) and bis(2,2-dimethyl [3,4] -1,3,2-dithiastannolo)biphenyl is obtained as a yellowish crystal (0.787 g, 1.37 mmol, 46%) (compound D). Physical properties of compound D: Melting point 239–240° C.: $^1$H NMR (400 MHz, CDCl$_2$) δ1.02 (s, 12H, CH$_3$), 7.08 (dd, j=2.0, 8.2 Hz, 2H, ArH), 7.47 (d, j=8.2 Hz, 2H, ArH), 7.64 (d, j=2.0 Hz, 2H, ArH), $^{13}$CNMR (101 MHz, CDCl$_3$), δ2.6, 122.9, 127.7, 130.0, 136.4, 137.0, 138.7; $^{119}$SnNMR (149 MHz, CDCl$_2$), δ188.7; IR (KBr) 144, 1258, 1110, 1027, 877, 800, 760, 665 cm$^{-1}$; MS (70 eV) m/z576 (M$^+$); Analytical calculated value, C$_{16}$H$_{18}$ S$_4$Sn$_2$: C, 33.36; H, 3.15%. Measured value: C, 33.44; H, 3.33%.

E. Synthesis of Subjected Compound 3,3',4,4'-tetramercaptobiphenyl (Process 5 of Schema 1: Deprotection Reaction)

Under the nitrogen gas atmosphere, hydrogen chloride gas generated from concentrated sulfuric acid and sodium chloride is blown in to the pre-dried THF solution (35 ml) of bis(2,2-dimethyl[3,4-d]-1,3,2-dithiastanolo)biphenyl for approximately 6 hours continuing monitoring. After confirmed that the substrate is disappeared, cooled down to the temperature of 0° C. and water is added. Deposited crystal is separated by suction filtration, and the obtained crystal is dried by vacuum heating (50° C.). Thus the subjected compound 3,3',4,4'-tetramercaptobiphenyl is obtained as a yellowish crystal (2.365 g, 2.24 mmol, 64%) (compound E). Physical properties of compound E: Melting point 97–100° C.: $^1$H NMR (400 MHz, CDCl$_3$) δ3.76 (s, 2H, SH), 7.22 (dd, j=2.0, 8.1 Hz, 2H, ArH), 7.40 (d, j=8.1 Hz, 2H, ArH), 7.52 (d, j=2.0 Hz, 2H, ArH), $^{13}$CNMR (101 MHz, CDCl$_3$), δ125.2, 129.2, 139.7, 131.4, 131.7, 138.3; IR (KBr) 2555 (SH) cm$^{-1}$.

Example for Use of Compound E;

This compound can be used as the recovering agent for gold particles and gold ion or cupper particles or cupper ion. This is based on the use of reactivity of sulfur containing group mentioned above.

Example for Use

Aqueous solution of gold (5 ppm) is heated to 30–50° C., then the solution prepared by dissolving compound E synthesized in Example 1 in THF is added to above mentioned aqueous solution. After stirred for a while, deposite is separated by filtration. The concentration of gold in the filtrated solution is measured by an atomic absorption spectrophotometer, and the result shows that gold is not detected.

That is, above result indicates that gold is reacted with the compound of the present invention and removed completely as the deposite.

Example 2

F. Synthesis of 4,4"-dichlorosulfonyl1,1':4',1"-terphenyl [Process 1 of Schema 1 (1-a): Chlorosulfonylation]

Under the nitrogen gas atmosphere, chloro sulfuric acid is diluted by adding chloro sulfuric acid (0.53 ml, 8 eq.) into methylene chloride (10 ml), and 1,1':4',1"-terphenyl (0.230 g, 1.0 mmol) is added gradually into a container in which diluted chloro sulfuric acid is contained keeping the temperature at 0° C., then stirred at the room temperature for 6 hours. The obtained reacted mixture is poured into brine, and deposited white insoluble is removed by suction filtration. Since the small amount of product is possible to be remained, the residue is washed well by methylene chloride. Then, this solution and the extracted solution are dried up using magnesium sulfate. Solvent is vaporized off under the vacuum condition, and the impurity is removed from the obtained crude product by isolating by a column chromatography (φ=50 mm, h=100 mm; CHCl$_3$). Thus, 4,4"-dichlorosulfonyl1,1':4',1"-terphenyl (0.288 g, 0.67 mmol, 67%) is obtained as a colorless crystal (compound F).

Physical properties of compound F; Melting point is higher than 244° C.; $^1$N NMR (400 MHz, CDCl$_3$) δ7.76 (s, 4H, ArH), 7.84–7.86 (m, 4H, ArH), 8.12–8.14 (m, 4H, ArH); $^{13}$CNMR (101 MHz, CDCl$_3$), δ 76.7, 77.0, 127.8, 128.3; IR (KBr) 1367, 1170 (SO$_2$) cm$^{-1}$.

G. Synthesis of 4,4"-dimercapto-1,1':4',1"-terphenyl (Process 1-b of Schema 2)

4,4"-dichlorosulfonyl1,1':4',1"-terphenyl (8.576 g, 20 mmol) synthesized in process 1-a is dissolved in tetrahydrofuran (THF) solvent (300 ml), add lithium aluminium hydride (8.586 g, 200 mmol, 10 eq.) and refluxed for 3 hours. The obtained reacted mixture is poured into ice water, and adjusted the pH to 1 or less by adding concentrated hydrochloric acid. Deposited impurity is removed by suction filtration, then washed by methylene chloride completely. After that, the filtrate is extracted by acid-base extraction (CH$_2$Cl$_2$, NaOH, HCl), the organic phase is dried up using magnesium sulfate and recrystalyzed. Thus, light yellowish crystal of 4,4"-dimercapto-1,1':4',1"-terphenyl (3.003 g, 10.2 mmol, 51%) is obtained (compound G).

Physical properties of compound G; Melting point is higher than 300° C.; $^1$N NMR (400 MHz, CDCl$_3$) δ3.47 (s, 2H, SH), 7.34–7.36 (m, 4H, ArH), 7.48–7.51 (m, 4H, ArH), 7.60–7.61 (m, 4H, ArH); $^{13}$CNMR (101 MHz, CDCl$_3$), δ127.3, 127.6, 130.0, 138.3, 139.5; IR (KBr) 2553 (SH) cm$^{-1}$.

H. Synthesis of 4,4"-bis(N,N-dimethylaminosulfonyl)-1,1': 4',1"-terphenyl (Process 2 of Schema 2)

4,4"-dichlorosulfonyl-1,1':4',1"-terphenyl (6.568 g, 14.7 mmol) which is synthesized in process 1 is dissolved into 300 ml of tetrahydrofuran solvent, add aqueous solution of dimethylamine (9.348 ml, 10.07 M, 4.8 eq.) and stirred for 3 hours at room temperature. Then, water is added to the reacting solution and stirred for 30 minutes. White deposit is separated by suction filtration, vacuum dried and recrystallized by chloroform. Thus, 4,4"-bis(N,N-dimethylaminosulfonyl)-1,1':4',1"-terphenyl (5.297 g, 11.9 mmol, 90%) is obtained as a colorless crystal (compound H).

Physical properties of compound H: Melting point 293–294° C.: $^1$H NMR (400 MHz, CDCl$_3$) δ2.27 (s, 12H, NMe$_2$), 7.73 (s, 4H, ArH), 7.77–7.79 (m, 4H, ArH); 7.86–7.88 (m, 4H, ArH); $^{13}$CNMR (101 MHz, CDCl$_3$), δ37.9, 127.5, 128.0, 128.4, 135.2, 139.5, 144.6; IR (KBr) 1337, 1163 (SO$_2$) cm$^{-1}$.

I. Synthesis of 3,3"-dimercapto-4,4"-bis(N,N-dimethylaminosulfonyl)-1,1':4',1"-terphenyl (Process 3 of Schema 2)

Under the nitrogen gas atmosphere, 4,4"-bis(N,N'-dimethylaminosulfonyl)-1,1',4',1"-terphenyl (10.787 g, 24.2 mmol) which is synthesized in process 2 is dissolved in absolute THF solution (100 ml), n-butyllithium (58.08 mmol, 2.4 eq.) is added and stirred for 3 hours at room temperature. Then, to the reacting solution, lithium aluminium hydride (4.592 g, 121 mmol, 50 eq.) is added and stirred for 2 hours at room temperature. The obtained reacted mixture is poured into ice water, and adjusted the pH to 1 or less by adding hydrochloric acid, that is, acidified. Yellowish deposit is removed by suction filtration, and the separated filtrate is washed by methylene chloride completely. After that, the filtrate is extracted by acid-base extraction (CH$_2$Cl$_2$, NaOH, HCl) for two times, and the separated organic phase is dried up using magnesium sulfate. Solvent is evaporated off under vacuum condition and the obtained crude product is isolated by a column chromatography (φ=50 mm, h=100 mm×2; CHCl$_3$: AcOEt=5:1), further refined by crystallization (CHCl$_3$) and 3,3"-dimercapto-4,4"-bis(N,N-dimethylaminosulfonyl)-1,1':4',1"-terphenyl (2.58 g, 5.1 mmol, 21%) is obtained as a light yellowish crystal (compound I).

Physical properties of compound I: Melting point 194° C.: $^1$H NMR (400 MHz, CDCl$_3$) δ2.88 (s, 12H, NMe$_2$), 4.85 (s, 2H, SH), 7.48 (dd, j=1.7, 8.3 Hz, 2H, ArH), 7.63 (d, j=1.7 Hz, 2H, ArH), 7.69 (s, 4H, ArH), 7.98 (d, j=8.3 Hz, 2H, ArH), $^{13}$CNMR (101 MHz, CDCl$_3$) δ37.6, 123.8, 127.8, 130.2, 131.9, 132.5, 134.7, 138.8, 144.5; IR (KBr) 1333, 1147 (SO$_2$), 2555 (SH) cm$^{-1}$; MS (70 eV) m/z508 (M$^+$); Anal. Calculated value, C$_{22}$H$_{24}$N$_2$O$_4$S$_4$: C, 51.94; H, 4.76, N, 5.51%. Measured value: C, 51.97; H, 4.77; N, 5.62%.

J. Synthesis of 3,3",4,4"-tetramercapto-1,1':4',1"-terphenyl (3-a, 3-b of Schema 2)

3,3"-dimercapto-4,4"-bis(N,N'-dimethylaminosulfonyl)-1,1':4',1"-terphenyl (508 mg, 1 mmol) synthesized in process 3-a is dissolved into 30 ml of absolute THF, lithium aluminium hydride (445 mg, 12 mmol, 12 eq) is added at the temperature of 0° C., then the reacting solution is refluxed for 24 hours. The obtained reaction mixture is poured into ice water, and adjusted the pH to 1 or less by adding hydrochloric acid, that is, acidified. Deposited green precipitate is removed by suction filtration, then the filtrate is washed by methylene chloride completely. After that, the filtrate is extracted by acid-base extraction (CH$_2$Cl$_2$), the separated organic phase is dried up using magnesium sulfate and recrystallized. Solvent is evaporated off under vacuum condition and the obtained crude product is isolated by a column chromatography (φ=20 mm, h=10 mm; AcOEt), further refined by recrystallization (CH$_2$Cl$_2$) and 3,3",4,4"-tetramercapto-1,1':4',1"-terphenyl (78 mg, 22%) is obtained as a light yellowish crystal (compound J).

Physical properties of compound J: Melting point 171–172° C.: $^1$H NMR (400 MHz, CDCl$_3$) δ3.78 (s, 2H, SH), 3.82 (s, 2H, SH) 7.34 (dd, j=1.9, 8.1 Hz, 2H, ArH), 7.45 (d, j=8.1 Hz, 2H, ArH), 7.60 (s, SH, ArH), 7.64 (d, j=1.9 Hz, 2H, ArH), IR (KBr) 2534 (SH) cm$^{-1}$ Example for Use of Compound J;

This compound can be used as the recovering agent for gold particles and gold ion or cupper particles or cupper ion. This is based on the use of reactivity of sulfur containing group mentioned above.

Example for Use

Aqueous solution of gold (5 ppm) is heated to 30–50° C., then the solution prepared by dissolving compound J synthesized in Example 2 in THF is added to the solution mentioned above. After stirred for a while, deposit is separated by filtration. The concentration of gold in the filtrated solution is measured by an atomic absorption spectrophotometer, and the result shows that gold is not detected.

That is, above result indicates that gold is reacted with the compound of the present invention and removed completely as the deposit.

INDUSTRIAL APPLICABILITY

As mentioned above, biphenyl, terphenyl characterizing two or three benzene rings are directly bonded, form a rigid structure and is expected to apply to a fast material. Further, by introducing to aromatic ring a thiol group which has reactivity, the functionality of a compound with sulfur containing groups can be further improved, and can use the compound with sulfur containing groups to impart functionality to the surface can be expected besides the concrete example for use mentioned above.

For example, uses of the compound with sulfur containing groups in an adhesive field or an electronic materials field can be expected.

The invention claimed is:

1. A novel tri- or tetra-thiol or thiolate of biphenyl, biphenyl derivatives, terphenyl or terphenyl derivatives represented by general formula A, general formula A

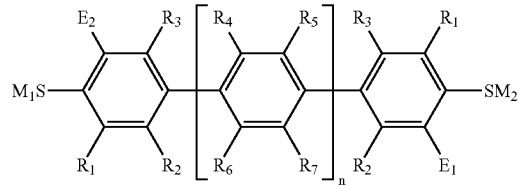

wherein, M$_1$ and M$_2$ are the groups selected independently from the group consisting of H, Na, Li and K, R$_1$–R$_7$ are the groups selected independently from the group consisting of H, substituted or not substituted alkyl group, substituted or not substituted phenyl group, naphthyl group, benzyl group, pyridyl group, substituted or not substituted alkoxy group, alkoxycarbonyl group, aldehyde group, nitroso group, nitro group, substituted or not substituted amino group, substituted or not substituted phenylazo group, alkylazo group, substituted or not substituted alkylthio group, substituted or not substituted phenylthio group, substituted or not substituted alkylsulfinyl group, phenylsulfinyl group, substituted or not substituted alkylsulfonyl group, phenyl sulfonyl group, divalent benzophenone residue, phenylether residue, alkylene group, cyclo alkylene group, pyridilene group, ester residue, carbonyl group and biphenylyl group, and $R_1$–$R_7$ on each phenyl group can be same or can be different, $E_1$ and $E_2$ are the groups selected independently from the group consisting of $SM_3$ and $SM_4$, wherein $M_3$ and $M_4$ are selected independently from the group consisting of the groups defining $M_1$ and $M_2$ mentioned above, or groups defining $R_1$–$R_7$ mentioned above, n is 1 or 0 and when n is 0, $E_1$ and $E_2$ are $SM_3$ and $SM_4$ and when n is 1 $E_1$ and/or $E_2$ is $SM_3$ and/or $SM_4$.

2. The tetra-thiol or tetra-thiolate included in the compound represented by general formula A of claim 1, wherein n is 0, $E_1$ and $E_2$ are $SM_3$ and $SM_4$ and $R_1$–$R_7$ are H.

3. The tri-thiol or tri-thiolate included in the compound represented by general formula A of claim 1, wherein n is 1, $E_1$ and $E_2$ are $SM_3$ and $SM_4$ and $R_1$–$R_7$ are H.

4. The tetra-thiol or tetra-thiolate included in the compound represented by general formula A of claim 1, wherein n is 1, $E_1$ and $E_2$ are $SM_3$ or $SM_4$ and $R_1$–$R_7$ are H.

5. A method for production of tetra-thiol or thiolate included in the compound represented by general formula A of claim 1 wherein n is 0, containing at least following processes (1) to (5);
(1) the process of synthesizing 4,4'-biphenyldisulfonylchloride or derivatives thereof by reacting $ClSO_3H$ with diphenyl at least whose 4, 4', 3 and 3' sites are H,
(2) the process of synthesizing 4,4"-bis(N,N'-dimethylaminosulfonyl)-biphenyl or derivatives thereof by reacting dimethylamine with the compound obtained by (1),
(3) the process of synthesizing 4,4'-bis(N,N'-dimethylaminosulfonyl)-3,3'-dimercapto biphenyl or derivatives thereof by reacting normal butyllithium with the compound obtained by (2), and further reacting simple substance of sulfur $S_8$ with the compound obtained by former process,
(4) the process of synthesizing bis(2,2-dimethyl[3,4-d]-1,3,2-dithiastanolo) biphenyl, and
(5) the process of reacting hydrogen chloride with bis(2,2-dimethyl [3,4-d]-1,3,2-dithiastanolo) biphenyl obtaind by (4).

6. The method for production of tetra-thiol or thiolate of claim 5, wherein biphenyl is unsubstituted biphenyl.

7. A method for production of terphenyl, tri- or tetra-thiol or thiolate included in the compound represented by general formula A in claim 1, whose 4, 4" and 3 and/or 3" are $SM_1$ and $SM_2$, $SM_3$ and/or $SM_4$, containing at least following processes (1) to (4);
(1) the process of synthesizing of 4,4'-terphenyldisulfonylchloride or derivatives thereof by reacting $ClSO_3H$ with terphenyl at least whose 4, 4" and 3 and/or 3" sites are H
(2) the process of synthesizing 4,4"-bis(N,N'-dimethylaminosulfonyl)-terphenyl or derivatives thereof by reacting dimethylamine with the compound obtained by (1),
(3) the process of synthesizing 4,4'-bis(N,N'-dimethylaminosulfonyl)-3, and/or 3"-mercapto or derivatives thereof by reacting normalbutyllithium with the compound obtained by (2), and further reacting simple substance of sulfur $S_8$ with the compound obtained by former process, and
(4) the process of reacting the compound obtained by (3) with lithium ammonium hydroxyde.

8. The method for production of tri- or tetra-thiol or thiolate of claim 7, wherein terphenyl is an unsubstituted terphenyl.

* * * * *